United States Patent
Kutyrev et al.

(10) Patent No.: US 12,129,233 B2
(45) Date of Patent: Oct. 29, 2024

(54) WATER-SOLUBLE SALTS OF CANNABINOIDS, PREPARATION AND USES THEREOF

(71) Applicants: Alexander Kutyrev, San Diego, CA (US); Tom Newman, San Diego, CA (US); Renat Kadyrov, Frankfurt am Main (DE)

(72) Inventors: Alexander Kutyrev, San Diego, CA (US); Tom Newman, San Diego, CA (US); Renat Kadyrov, Frankfurt am Main (DE)

(73) Assignee: Aurora Fine Chemicals LLC, San Diego, CA (US)

( * ) Notice: Subject to any disclaimer, the term of this patent is extended or adjusted under 35 U.S.C. 154(b) by 0 days.

(21) Appl. No.: 17/705,267

(22) Filed: Mar. 25, 2022

(65) Prior Publication Data

US 2022/0332694 A1    Oct. 20, 2022

Related U.S. Application Data

(60) Provisional application No. 63/205,654, filed on Apr. 7, 2021.

(51) Int. Cl.
*C07D 311/80*  (2006.01)
*C07C 39/19*   (2006.01)
*C07C 39/23*   (2006.01)

(52) U.S. Cl.
CPC ............ *C07D 311/80* (2013.01); *C07C 39/19* (2013.01); *C07C 39/23* (2013.01); *C07C 2601/16* (2017.05)

(58) Field of Classification Search
CPC .............................. C07D 311/80; C07C 39/19
See application file for complete search history.

(56) References Cited

U.S. PATENT DOCUMENTS 10,941,102 B2 *  3/2021  Wohleb ................ B01D 9/0054

OTHER PUBLICATIONS

Kozlowska et al (2007): STN International CAPLUS database (Columbus, Ohio), Accession No. 2007: 1130820.*
Wohleb et al (2019): STN International CAPLUS database (Columbus, Ohio), Accession No. 2019: 2266195.*
Vega Jose (2020): STN International CAPLUS database (Columbus, Ohio), Accession No. 2020: 512490.*
Dimnik Maximo (2019): STN International CAPLUS database (Columbus, Ohio), Accession No. 2019: 556545.*

* cited by examiner

*Primary Examiner* — Golam M Shameem

(57) ABSTRACT

The novel water-soluble salts of cannabinoids with increased bioavailability, their preparation and uses.

2 Claims, No Drawings

WATER-SOLUBLE SALTS OF CANNABINOIDS, PREPARATION AND USES THEREOF

The novel salts of cannabinoids with increased water solubility, their preparation and uses.

BACKGROUND

Cannabinoids are terpenophenolic compounds found in plants comprising *Cannabis sativa, C. indica,* and *C. Mderalis* belonging to the Cannabaceae family. *Cannabis* plants have been cultivated for a variety of uses including making fibers (hemp), medicinal use and recreational drug use.

Cannabinoids are targeting cannabinoid receptors in humans. The well-known cannabinoids presented in high concentrations in *Cannabis sativa* are tetrahydracannabinolacid (THCA), its decarboxylated product tetrahydracannabinol (THC) and cannabidiolic acid (CBDA) and its decarboxylated product cannabidiol (CBD).

The cannabinoids have a variety of pharmacological benefits and used for treating a wide range of medical conditions. THC has psychoactive calming effect, also is analgesic, antioxidant and appetite enhancer. CBD has neuroprotective effects and ameliorative effects in patients with Parkinson's disease and schizophrenia.

Cannabinoids were found to be effective by treatment glaucoma, AIDS, neuropathic pain, spasticity associated with multiple sclerosis, fibromyalgia and chemotherapy-induced nausea. They are also effective in the treatment of allergies, inflammation, infection, epilepsy, depression, migraine, bipolar disorders, anxiety disorder, drug dependency and drug withdrawal syndromes. Additionally, some cannabinoids are potent antioxidant and anti-inflammatory compounds known to provide protection against acute and chronic neurodegeneration.

It is well known that aqueous solubility is a key parameter influencing biological activity and frequently the rate-limiting step in gastrointestinal absorption of a drug. Irrespective of the intended route of administration the active substance needs to be dissolved or solubilized in aqueous media at least at some point, to become bioavailable or applicable to the patient. For instance, active substance in orally administered tablets should be dissolved in the gastrointestinal fluids.

The main disadvantage of cannabinoids is their low oral bioavailability. The low bioavailability is due to low water solubility in combination with an extensive first-pass metabolism.

The salification of an active pharmaceutical ingredient is the most common method to improve its aqueous solubility and bioavailability. Generally, the pharmaceutical industry has increasingly used the salification process to enhance the properties of drug products, and today more than 50% of the drugs on the market are sold as salts. Sales success is due to ease of synthesis, relatively simple purification through crystallization, and reliability of the salts. Widespread use of salts is not limited to the solubility and dissolution rate, but rather it affects several pharmacological and technological aspects, as impurity profile, physicochemical stability, manufacturability and toxicity.

It seems legit that ionizable species like salts will be more soluble in water and thus give a better chance to reach the biological target, regardless of the required administration routes, intravenous, oral Intramuscular, subcutaneous etc.

Cannabinoids occur in the plant *Cannabis sativa* in the form of their carboxyl derivatives, the carmabinoid carboxylic acids. Their salts could be produced by adding organic/inorganic bases. U.S. Pat. No. 9,376,367 discloses soluble salts of cannabinoid carboxylic acids by treatment with a suitable inorganic or organic bases.

Most of the cannabinoid acids are devoid of psychotropic effects and must be decarboxylated to the phenolic cannabinoids to provide *cannabis*-like therapeutic effects. In general, most phenols are responsible for the medicinal effects. (F. Grotenhermen, Clinical Phanacokinetics of Cannabinoids, J. Cannabis Ther. 2003(1), 3-51).

The salts of phenolic cannabinoids are almost ideal water-soluble cannabinoid prodrugs. It would be a significant achievement to provide salts of phenolic cannabinoids that are able to improve the bioavailability of active cannabinoids.

SUMMARY OF INVENTION

The inventors provide the water-soluble salts of phenolic cannabinoids that overcome the problem of insolubility of cannabinoids in water and associated low bioavailability.

The compounds of the present disclosure are defined as formula (I),

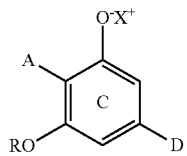

wherein the combination of A, D and R of moiety C form a cannabinoid and $X^+$ is selected from the group consisting of $NH_4^+$, mono, di or trivalent metal cations, organic cations including primary, secondary, tertiary or quaternary organic ammonium ions with up to 48 C-atoms, which can carry even more functional groups, hydrazinium ion ($N_2H_5^+$), hydroxylammonium ion ($NH_3OH^+$), guanidinium ion ($CN_3H_6^+$), and organic derivatives of pyridinium, imidazolinium, imidazolium, tetrahydropyrimidinium and 1,3-diazepan-ylidenium cations, which can carry even more functional groups, and Y is selected from the group consisting of hydrogen or $COO^-X^+$.

Examples of phenolic cannabinoids shown on the scheme 1 are the following: Cannabigerol (CBG-$C_5$), Cannabigerovarin (CBGV-$C_3$), Cannabigerol Monomethylether (CBGM-$C_5$), Cannabichromen (CBC-$C_5$), Cannabichromevarin (CBC-$C_3$), Cannabidiol (CBD-$C_5$), Cannabidiol-C4 (CBD-$C_4$), Cannabidivarin (CBDV-$C_4$), Cannabidiorcol (CBD-C1), Cannabinodiol (CBND-C5), Cannabinodivarin (CBND-C3), Cannabidiolic acid (CBDA), Cannabigerolic acid, $\Delta^8$-Tetrahydrocannabinol ($\Delta^8$-THC-C5), $\Delta^9$-Tetrahydrocannabinol ($\Delta^9$-THC-$C_5$), $\Delta^9$-Tetrahydrocannabinol-$C_4$ ($\Delta^9$-THC-$C_4$), $\Delta^9$-Tetrahydrocannabivarin ($\Delta^9$-THCV-$C_3$), $\Delta^9$-Tetrahydrocannabiorcol ($\Delta^9$-THCO-$C_1$), Tetrahydrocannabinolic acid, Cannabinol (CBN-C5), Cannabinol-C4 (CBN-C4), Cannabivarin (CBN-C3), Cannabinol-C2 (CBN-C2), Cannabiorcol (CBN-C2), 10-Oxo-$\Delta$ 6a(10a)-tetrahydrocannabinol (OTHC), 6a, 7,10a-Trihydroxy-$\Delta^9$-tetrahydrocannabinol (Cannabitetrol), Cannabitriol (CBT-C5), Cannabitriol-C3 (CBT-C3), Cannabiripsol (Cannabiripsol-C5), 8,9-Dihydroxy-$\Delta^{6a(10a)}$-tetrahydrocannabinol (8,9-Di-OH-CBT-$C_5$), Cannabielsoin (CBE-$C_5$), $C_3$-Cannabielsoin (CBE-$C_3$), Cannabiglendol-C3 (OH-iso-HHCV-$C_3$), Dehydrocannabifuran (DCBF-$C_5$), Cannabifuran (CBF-$C_5$), $\Delta^7$-Isotetrahydrocannabinol, Cannabichromanon (CBCN- C$_5$), Cannabichromanon-C$_3$ (CBCN-C$_3$), Cannabicyclol (CBL-C$_5$), Cannabicyclovarin (CBLV-C$_3$).

In certain embodiments, the compounds of the present invention or the stereoisomers thereof are in crystalline form, in amorphous form, or are in solution.

In certain embodiments, the phenolic cannabinoids could be selected from the group consisting of Cannabigerol, Cannabigerovarin, Cannabigerol Monomethylether, Cannabichromen, Cannabichromevarin, Cannabidiol, Cannabidiol-C4, Cannabidivarin, Cannabidiorcol, Cannabinodiol, Cannabinodivarin, Cannabidiolic acid (CBDA), Cannabigerolic acid, Tetrahydrocannabinolic acid, $\Delta^8$-Tetrahydrocannabinol, $\Delta^9$-Tetrahydrocannabinol, $\Delta^9$-Tetrahydrocannabinol-C$_4$, $\Delta^9$-Tetrahydrocannabivarin, $\Delta^9$-Tetrahydrocannabiorcol, Cannabinol, Cannabinol-C4, Cannabivarin, Cannabinol-C2, Cannabiorcol, 10-Oxo-$\Delta$ 6a(10a)-tetrahydrocannabinol, 6a, 7,10a-Trihydroxy-$\Delta^9$-tetrahydrocannabinol, Cannabitriol, Cannabitriol-C3, Cannabiripsol, 8,9-Dihydroxy-$\Delta^{6a(10a)}$-tetrahydrocannabinol, Cannabielsoin, C$_3$-Cannabielsoin, Cannabiglendol-C3, Dehydrocannabifuran, Cannabifuran, $\Delta^7$-Isotetrahydrocannabinol, Cannabichromanon, Cannabichromanon-C$_3$, Cannabicyclol, Cannabicyclovarin and a mixture thereof.

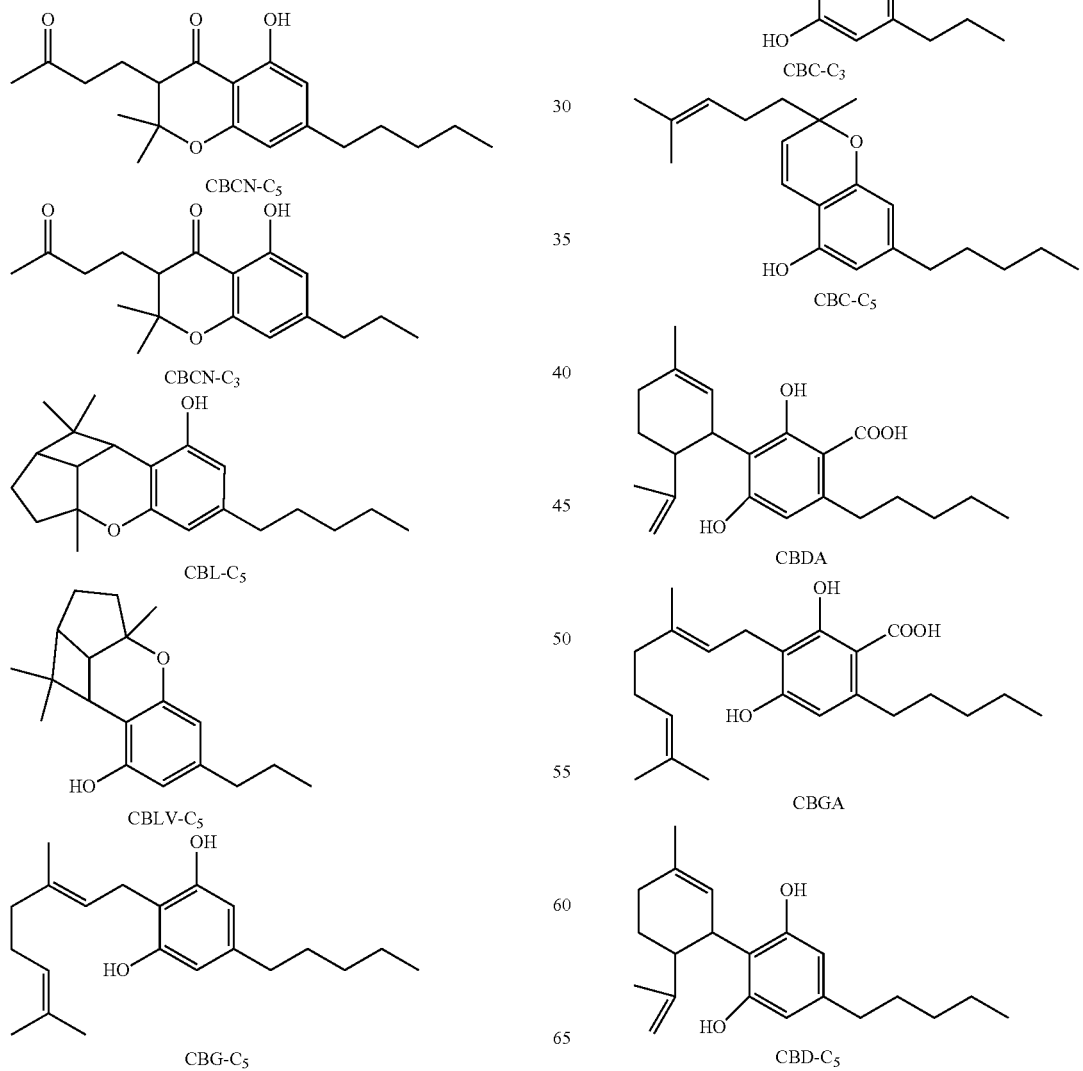

Scheme 1. Examples of phenolic cannabinoids

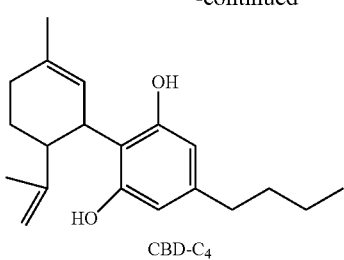
CBD-C₄
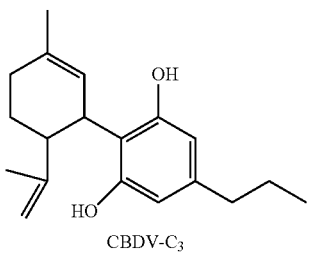
CBDV-C₃
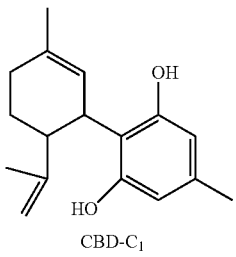
CBD-C₁
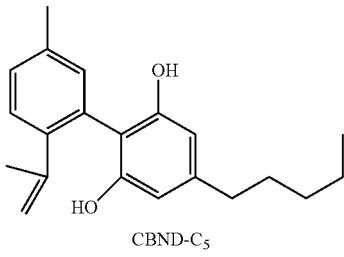
CBND-C₅
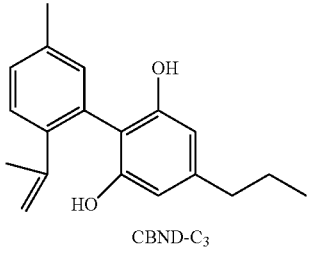
CBND-C₃
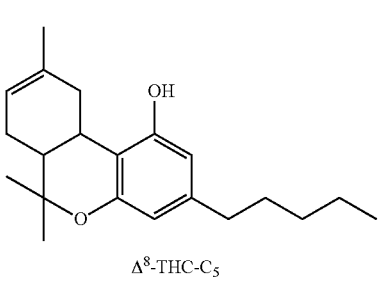
Δ⁸-THC-C₅
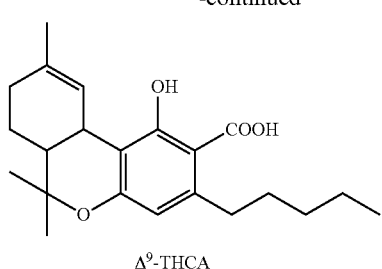
Δ⁹-THCA
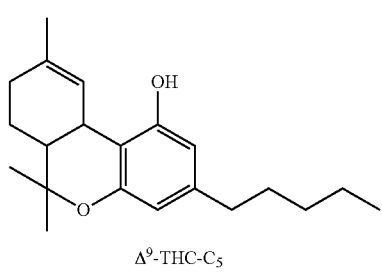
Δ⁹-THC-C₅
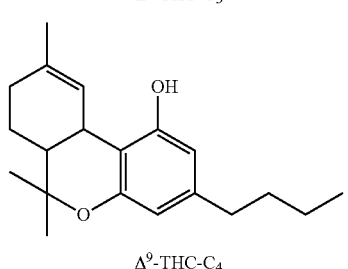
Δ⁹-THC-C₄
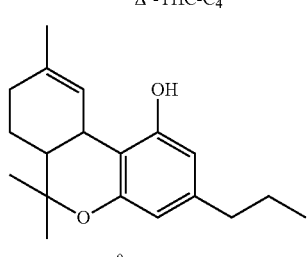
Δ⁹-THCV-C₃
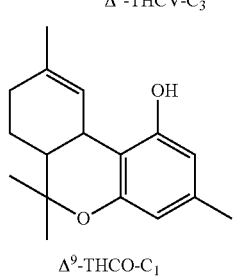
Δ⁹-THCO-C₁
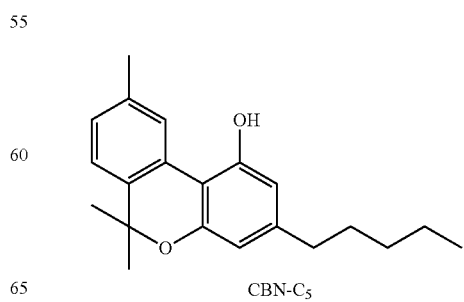
CBN-C₅

-continued
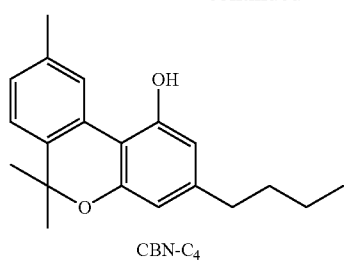
CBN-C4
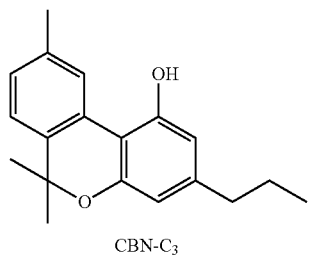
CBN-C3
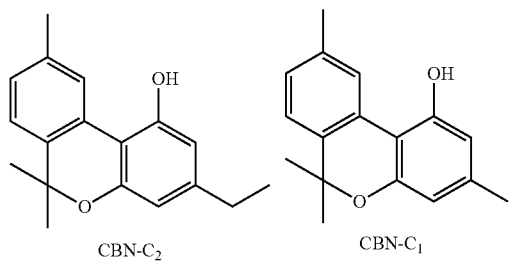
CBN-C2              CBN-C1
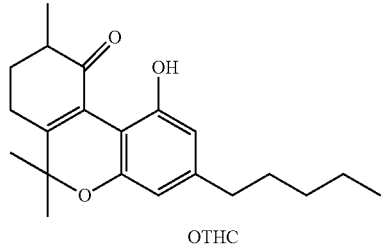
OTHC
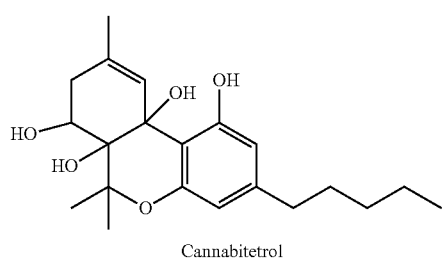
Cannabitetrol
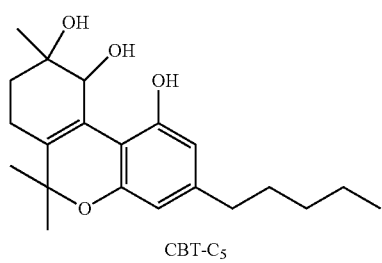
CBT-C5
-continued
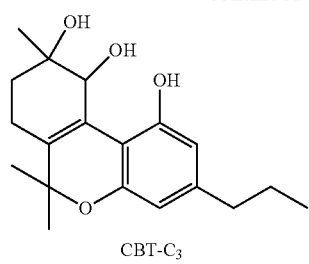
CBT-C3
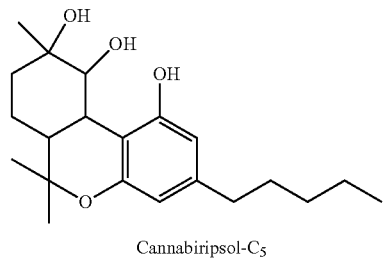
Cannabiripsol-C5
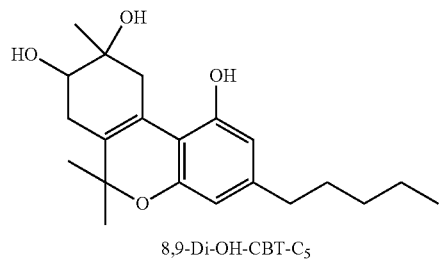
8,9-Di-OH-CBT-C5
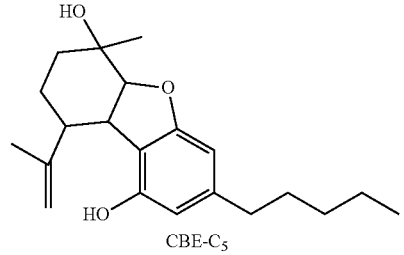
CBE-C5
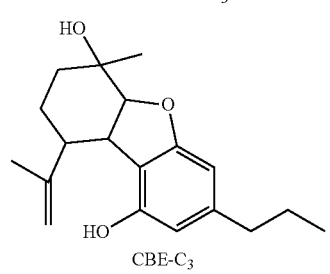
CBE-C3
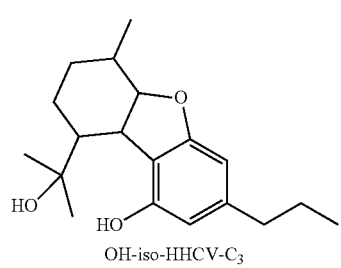
OH-iso-HHCV-C3

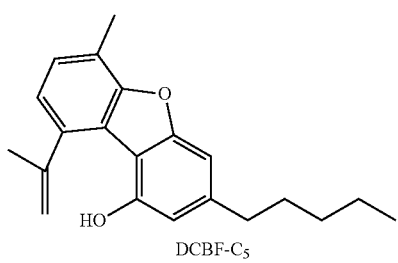

DCBF-C$_5$

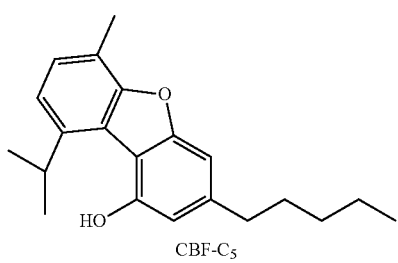

CBF-C$_5$

In the compounds and compositions of the disclosure as described herein, the organic cations may also have one or more functional groups.

The cations X$^+$ of the salts and compositions of the disclosure as described herein may also be primary, secondary, tertiary or quaternary organic ammonium ions and ammonium ions have one or more functional groups.

Examples of amines that can form phenolic salts with non-carboxylic cannabinoids are shown on the schemes 2 and 3.

Scheme 2. Examples of amines of low and medium basicity.

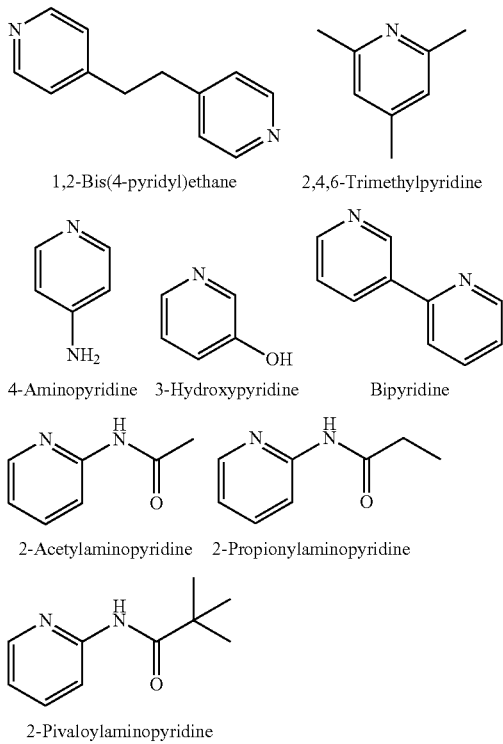

1,2-Bis(4-pyridyl)ethane    2,4,6-Trimethylpyridine

4-Aminopyridine  3-Hydroxypyridine    Bipyridine

2-Acetylaminopyridine  2-Propionylaminopyridine

2-Pivaloylaminopyridine

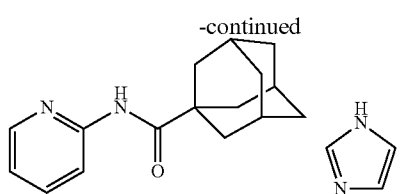

2-Adamantylaminopyridine    Imidazole

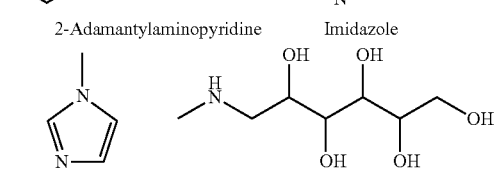

N-Methylimidazole    N-Methylglucamine

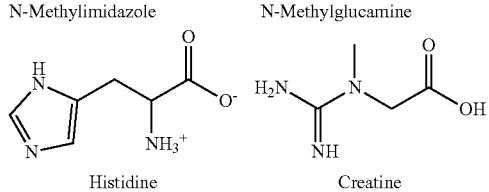

Histidine    Creatine

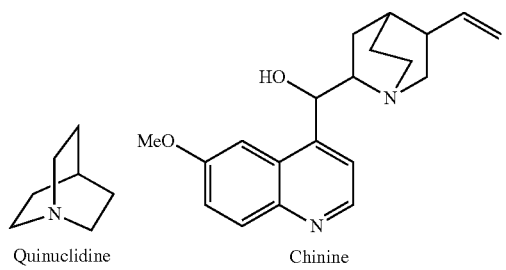

Quinuclidine    Chinine

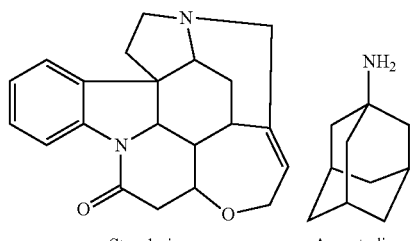

Strychnine    Amantadine

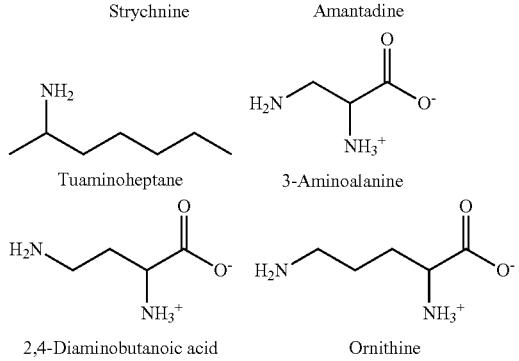

Tuaminoheptane    3-Aminoalanine 2,4-Diaminobutanoic acid    Ornithine

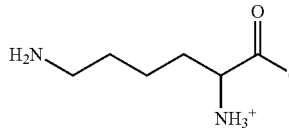

Lysine

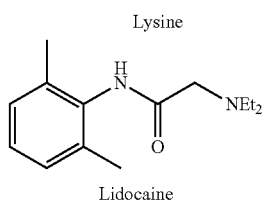

Lidocaine

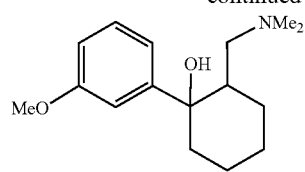
Tramadol

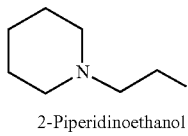
2-Piperidinoethanol

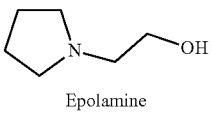
Epolamine

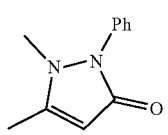
Phenazone

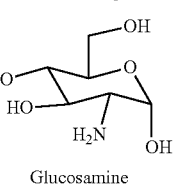
Glucosamine

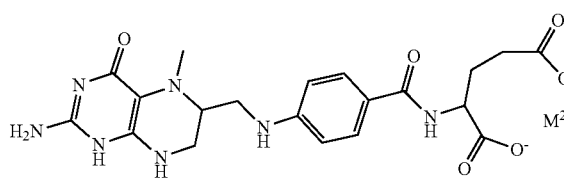
Levomefolate calcium (M = Ca) or magnesium (M = Mg)

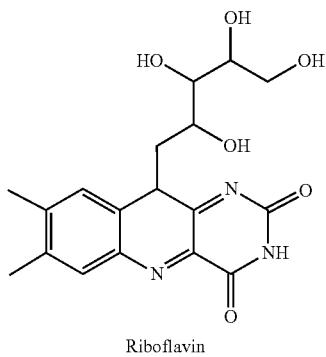 [SMILES: Cc1cc2c(cc1C)C(CC(O)C(O)C(O)CO)C1=NC(=O)NC(=O)C1=N2]
Riboflavin

Scheme 3. Examples of amines of high basicity

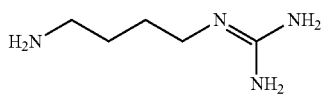
Agmatine

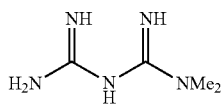
Metformin

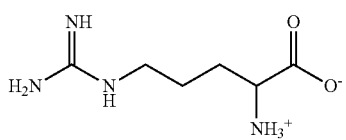
Arginine

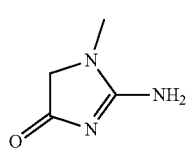
Creatinine

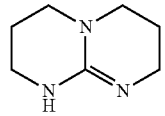
1,5,7-Triazabicyclo(4.4.0)dec-5-ene

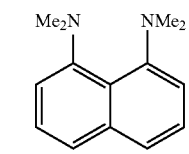
1,8-Bis(N,N-dimethylamino)naphthalene

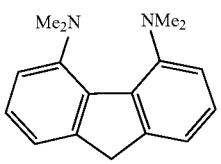
4,5-Bis(dimethylamino)-fluorene

Examples of organic cations in the phenolic salts of non-carboxylic cannabinoids are shown on scheme 4.

Scheme 4. Examples of organic cations $R_4N^+$

Tetraalkyl/arylammonium

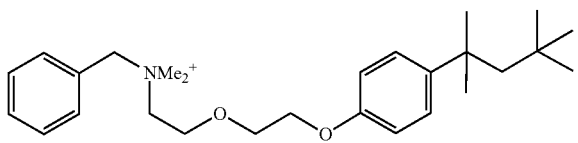
Benzethonium

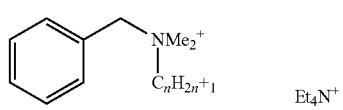
Benzalkonium    Tetraethylammonium

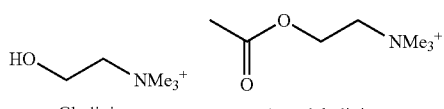
Cholinium    Acetylcholinium

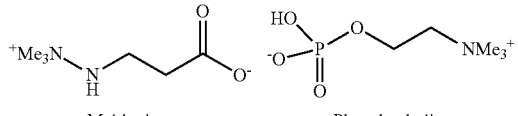
Meldonium    Phosphocholine

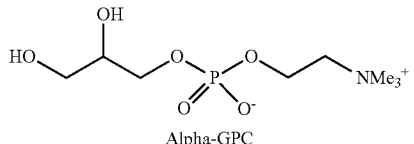
Alpha-GPC

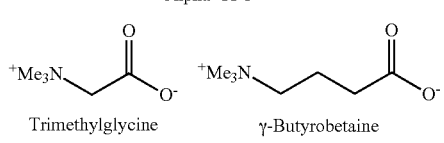
Trimethylglycine    γ-Butyrobetaine

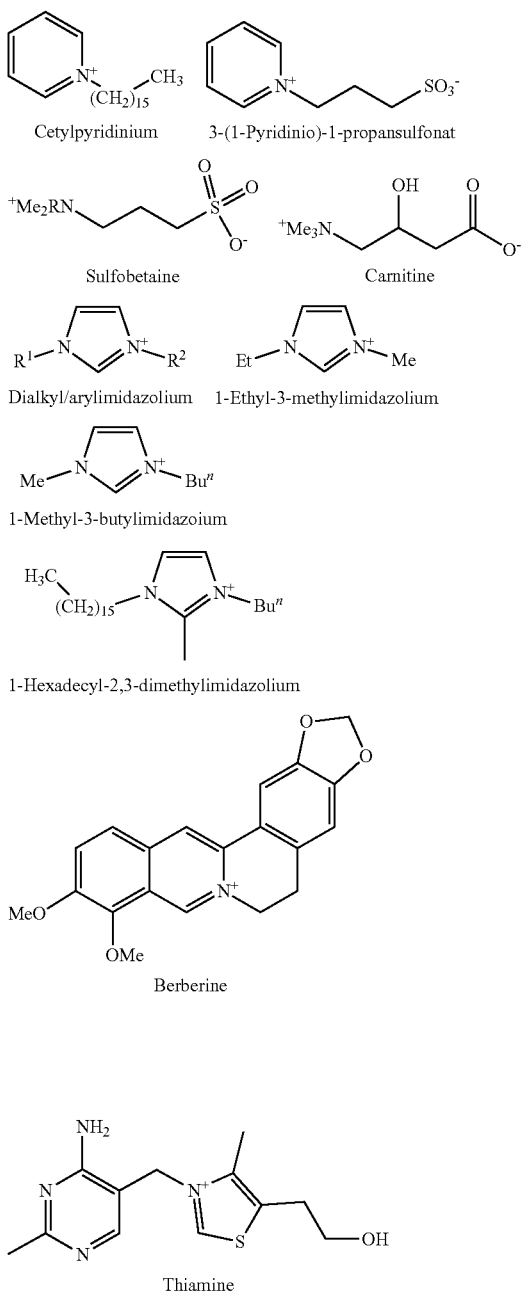

Cetylpyridinium
3-(1-Pyridinio)-1-propansulfonat
Sulfobetaine
Carnitine
Dialkyl/arylimidazolium
1-Ethyl-3-methylimidazolium
1-Methyl-3-butylimidazoium
1-Hexadecyl-2,3-dimethylimidazolium
Berberine
Thiamine Aminoglycosides can act as amines forming phenolic salts of non-carboxylic cannabinoids.

Examples of aminoglycosides are the following: 1-amino-1-deoxy-D-ribitol, 1-(benzylamino)-1-deoxy-L-arabinitol, 1-amino-1-deoxy-D-fructose, 1-deoxy-1-morpholino-D-fructose, 1-deoxy-1-(4-toluidino)hex-2-ulose, 1-deoxy-1-(p-toluidino)-beta-D-glucopyranose, 2-deoxy-N-phenylpentofuranosylamine, 2-amino-2-deoxy-beta-D-glucopyranose, $N^6$-(1-deoxy-D-fructos-1-yl)-L-lysine, steptamine, 2-desoxysteptamine, steptidine, actinamine, A second aspect of the invention is a process of preparation the compounds of formula (I) as defined above, which comprises deprotonation of the phenolic hydroxyl group by addition of strong base B:

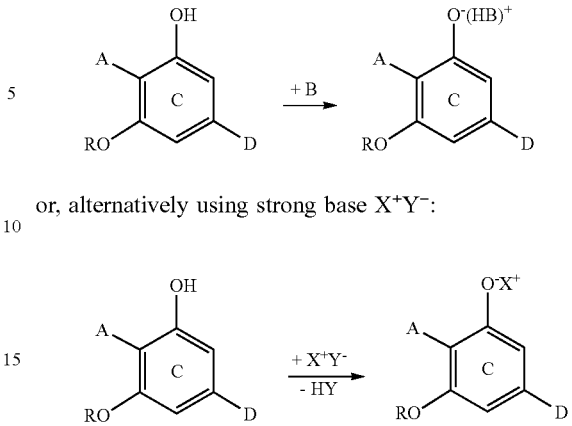

or, alternatively using strong base $X^+Y^-$:

The strong base B is defined as base with an association constant $pK_b$ less than 1.4, corresponding to $pK_a$ greater than 12.6.

The term "base" includes inorganic and organic base. The term "inorganic base" broadly refers to an inorganic compound that can act as a proton acceptor. The term "organic base," as used herein, also broadly refers to an organic compound that can act as a proton acceptor.

$X^+$ can be ammonium ions produced by action of acids on amines. Preferred are strong mineral acids.

Suitable acid is the hydrogen chloride.

The term "alkyl/aryl ammonium" refers to $NR^1R^2R^3R^4$ cation, where $R^1$, $R^2$, $R^3$ and $R^4$ are independently selected from hydrogen, 1-18 carbon atom straight or branched chain alkyl and alkenyl groups and aryl groups having up to 8 carbon atoms.

$X^+$ can also be the cation of compounds with at least one basic nitrogen atom, for example 1,2-bis(4-pyridyl)ethane, 2,4,6-trimethylpyridine, 4-aminopyridine, 3-hydroxypyridine, 2,2'-bipyridine, 2-acetylaminopyridine, 2-propionylaminopyridine, 2-pivaloylaminopyridine, 2-adamantylaminopyridine, imidazole, N-methylimidazole, 2-piperidinoethanol, 1,5,7-triazabicyclo(4.4.0)dec-5-ene, 1,8-bis(N,N-dimethylamino)naphthalene, 4,5-bis(dimethylamino)-fluorene, N-methylglucamine, quinuclidine, 3-aminoalanine, 2,4-diaminobutanoic acid, ornithine or an enantiomers thereof.

$X^+$ can also be the cation of substance with at least one basic nitrogen atom, for example histidine, creatine, chinine, strychnine, amantadine, tuaminoheptane, lysine, lidocaine, tramadol, epolamine, phenazone, agmatine, metformin, arginine, creatinine, morphine, methadone, hydromorphone or an enantiomers thereof.

Alternatively $X^+$ can be prepared from amines by quaternization. Therein the amine is combined with alkylating agent to achieve alkylation of the amino function. Methylation are the preferred forms of quaternization. Suitable methylation agents are the methyl halides and methyl sulfate.

A solvent may be employed for quaternization reaction. Preferably the solvent is an aprotic one. Solvents within the aprotic category include acetonitrile, acetone, ethers, toluene and $C_4$-$C_{10}$ hydrocarbons.

$X^+$ can be a pharmaceutical active cations, for example benzethonium, benzalkonium, cholinium, acetylcholinium, phosphocholine, alpha-GPC, trimethylglycine, meldonium, cetylpyridinium, 3-(1-pyridinio)-1-propansulfonat, sulfobetaine, α-butyrobetaine, 1-hexadecyl-2,3-dimethylimidazolium.

The cations X⁺ can be prepared from nutrient compounds includes vitamins, minerals, fiber and amino acids. Dietary supplements can also contain substances that have been confirmed as being essential to life and also marketed as having a beneficial biological effect, such as 4-aminobenzoic acid (also known as PABA), adenosylcobalamin (also known as cobamamide and dibencozide), acetyl-L-carnitine, folate (also known as vitamin $B_9$ and folacin), (6S)-5-methyltetrahydrofolate calcium, magnesium and glucosamine salts; melatonin, niacin (also known as nicotinic acid), nicotinamide, pyrroloquinoline quinone disodium salt, pyridoxine, pyridoxine 5'-phosphate, pyridoxal, pyridoxal 5'-phosphate, pyridoxamine, pyridoxamine 5'-phosphate, pyritinol, phosphatidylcholine, phosphatidylethanolamine, phosphatidylinositol, phosphatidylserine, riboflavin, thiamin, taurine, zinc picolinate and salts of uridine monophosphate.

The following amino acids can be used for a preparation cations X⁺: alanine, arginine, glycine, histidine, hydroxylysine, hydroxyproline, isoleucine, leucine, lysine, methionine, phenylalanine, proline, serine, theanine, threonine, tryptophan, tyrosine, valine and their salts, including all stereoisomers.

In step of deprotonation of the phenolic hydroxyl group by addition of base B disclosed herein, a base may be inorganic base selected from the group of metal hydrides, metal or ammonium hydroxides, metal alkoxides, metal amides or metal alkyls, wherein the inorganic base may be selected from the group of ammonium hydroxide and ammonium metal alkoxide.

In certain embodiments, the organic base may be selected from the group of agmatine, arginine, creatinine and metformin and the stereoisomers thereof and guanidine and their derivatives.

In certain embodiments, the organic base may be selected from the group of hydroxides and alkoxides of organic cations.

The organic cation X⁺ of the disclosure as described herein may be selected from the group of primary, secondary, tertiary or quaternary organic ammonium ions with up to 48 C-atoms, which can carry even more functional groups, hydrazinium ion ($N_2H_5^+$), hydroxylammonium ion ($NH_3OH^+$), guanidinium ion ($CN_3H_6^+$), and organic derivatives of pyridinium, imidazolinium, imidazolium, tetrahydropyrimidinium and 1,3-diazepan-ylidenium cations, which can carry even more functional groups.

The acidic to medium basic salts $X^+Z^-$ with $pK_a$ below 12.6 can be converted into strong base $X^+Y^-$ by anion exchange reaction:

$$X^+Z^- + M^+Y^- \rightarrow X^+Y^- + M^+Z^-$$

The cations M⁺ are selected from the group consisting of mono, di or trivalent metal cations.

Preferably, cations are selected from the group consisting of lithium, sodium, potassium, silver and barium.

Strong basic resins can be used to replace anion $Z^-$ by hydroxide anion.

The anion $Y^-$ can be organic or inorganic. Typical examples are hydride ion, hydroxide ion, alkoxide ion, amide anion, alkyl anion and the like.

The salts disclosed herein can be made using procedures familiar to the person of ordinary skill in the art and as described herein. One of skill in the art can adapt the reaction conditions and solvents used to fit the desired target molecule. Additionally, one skilled in the art would recognize that salts of the disclosure can be synthesized using different procedures altogether. For example, the person of ordinary skill in the art may adapt the procedures described herein and/or other procedures familiar to the person of ordinary skill in the art to make the salts described herein.

The procedure can involve heating the first reaction mixture at a suitable temperature to result in the first reaction mixture reaching a temperature from 25° C. to 170° C. In some embodiments, a ratio of cannabinoid to base used in the method can range from 1:0.5 to 1:5. In some embodiments, the starting materials are dissolved in a solvent and mixed with each other. Suitable solvents can be, but are not limited to, non-polar solvents like pentane, hexane, benzene, toluene, chloroform, diethyl ether, tert-butyl methyl ether, 1,4-dioxane and the like, including any and all combinations thereof; polar protic solvents like water, methanol, ethanol, propanol including any isomers thereof, butanol including any isomers thereof, formic acid, acetic acid, nitromethane, and the like, including any and all combinations thereof; aprotic polar solvents like acetone, dichloromethane, 1,2-dichloroethene, tetrahydrofuran, ethyl acetate, acetonitrile, dimethylformamide, dimethyl sulfoxide chlorobenzene, and the like, including any and all combinations thereof.

The reaction mixture can then be exposed to any pH range from 1 up to 14.

In yet additional embodiments, the procedure can further comprise a crystallization procedure. In some embodiments, crystallization includes mixing the filtered solution or the solution obtained from redissolving the product in the solvent mixture to thereby induce crystallization. In yet additional embodiments, the crystallization procedure can further comprise a seeding step whereby one or more seed crystals are added. In some embodiments utilizing a seeding step, the seed crystals can be added in an amount ranging from 0.1 wt % to 2 wt % based on the weight of cannabinoid present in the composition to which the seed crystals are added. The resulting solid can be isolated using a filtration or centrifugation step and then can be washed with a solvent. Any number of washing steps can be used, from one to ten and even more washing steps.

The salts of phenolic cannabinoids described above are water soluble. The water solubility offers the advantages when mixing and applying cannabinoids. The cannabinoids of this invention would be dissolved in water in an effective proportion, as may be easily determined by those skilled in the art. Because of their water solubility, the compounds of this invention also offer clinical advantages in the administration to reduce cannabinoid levels in humans and animals.

Cannabinoids have been found to have antioxidant properties, unrelated to NMDA receptor antagonism. This new found property makes cannabinoids useful in the treatment and prophylaxis of wide variety of oxidation associated diseases, such as ischemic, age-related, inflammatory and autoimmune diseases. The cannabinoids are found to have particular application as neuroprotectants, for example in limiting neurological damage following ischemic insults, such as stroke and trauma, or in the treatment of neurodegenerative diseases, such as Alzheimer's disease, Parkinson's disease and HIV dementia (U.S. Pat. No. 6,630,507B1). Cannabinoids can be used to treat inflammatory diseases (U.S. Pat. No. 6,410,588B1). Cannabidiol (CBD) uses for the treatment of severe and refractory graft versus host disease (GVHD) (U.S. Pat. No. 9,889,100 B2). GB2554592, claiming THC and CBD for use in the treatment of a glioma. GB2504263 claims CBD for preventing brain injury in newborns and GB2495841, claims CBD for the treatment of breast cancer. Generally, canabinoids are used in different type of cancer: prostate, breast, skin, glioma, colon, lung or a bone or lymph metastasis (U.S. Pat. No. 8,790,719B2, US20130059018, U.S. Ser. No. 10/758, 514B2).

Specifically, the water-soluble cannabinoids by the instant invention are expected to be an utility in the treatment of myasthenia gravis, to prevent as well as to treat infection by SARS-CoV-2, neurological and ophthalmological disorders, in miotic induction and in the reversal of drug-induced extrapyramidal symptoms which accompany psychiatric drug therapy, for the treatment of a medical condition, wherein the medical condition is selected from the group consisting of: nausea, vomiting, emesis, pain, wasting syndrome, HIV-wasting, chemotherapy induced nausea and vomiting, alcohol use disorders, dystonia, multiple sclerosis, inflammatory bowel disorders, arthritis, dermatitis, Rheumatoid arthritis, Crohn's disease, ulcerative colitis, irritable bowel syndrome (IBS), systemic lupus erythematosus (SLE), cutaneous lupus erythematosus, psoriasis, systemic lupus erythematosus. Type I diabetes (IDDM), Sjogren's disease, autoimmune thyroid disease, acquired immunodeficiency syndrome (AIDS), sarcoidosis, autoimmune uveitis, autoimmune hepatitis, hypersensitivity lung diseases, hypersensitivity pneumonitis, delayed-type hypersensitivity, interstitial lung disease (ILD) (e.g., idiopathic pulmonary fibrosis, or ILD associated with rheumatoid arthritis or other inflammatory diseases). Anti-inflammatory, anti-convulsant, anti-psychotic, anti-oxidant, neuroprotective, anti-cancer, immunomodulatory effects, peripheral neuropathic pain, neuropathic pain associated with post-herpetic neuralgia, diabetic neuropathy, shingles, burns, actinic keratosis, oral cavity sores and ulcers, post-episiotomy pain, psoriasis, pruritis, contact dermatitis, eczema, bullous dermatitis herpetiformis, exfoliative dermatitis, mycosis fungoides, pemphigus, severe erythema multiforme (e.g., Stevens-Johnson syndrome), seborrheic dermatitis, ankylosing spondylitis, psoriatic arthritis, Reiter's syndrome, gout, chondrocalcinosis, joint pain secondary to dysmenorrhea, fibromyalgia, musculoskeletal pain, neuropathic-postoperative complications, polymyositis, acute nonspecific tenosynovitis, bursitis, epicondylitis, post-traumatic osteoarthritis, synovitis, juvenile rheumatoid arthritis and inhibition of hair growth. Graves ophthalmopathy, amyotrophic lateral sclerosis (ALS), primary biliary cirrhosis, ileitis, chronic inflammatory intestinal disease, celiac disease, Alzheimers's disease, prion associated disease and cancer metastases.

In addition, the compounds of the present disclosure may be used in veterinary medicine for miotic action and for alleviation of colic in horses, as well as, for parallel diseases to those observed in humans, for which human efficacy is known. An effective amount of inhibitor to treat the above abnormalities may be determined on a case-by-case basis, by those skilled in the art associated with the particular use.

The compounds and compositions of the disclosure as described herein may be also used in the preparation of a medicament for the treatment of a medical condition, disease or disorder associated with inflammation.

In certain embodiments, the compounds of the present invention may be used for the treatment or prevention of a disease associated with a cannabinoid receptor.

The disclosure also relates to methods of treating or preventing a disease associated with cannabinoid receptor in a subject in need thereof, the method comprising administering to the subject a therapeutically effective amount of a compound according formulae 1 or a compositions thereof.

EXAMPLES

The preparation of the compounds of the disclosure is illustrated further by the following examples, which are not to be construed in any way as limiting the disclosure in scope or spirit to the specific procedures and compounds described in them. These examples are offered to illustrate the invention.

Choline Salt with CBD (1:1)

To a 50-mL Erlenmeyer flask equipped with drying tube ($CaCl_2$) commercially available choline chloride (476 mg, 3.4 mmol), KOH (196 mg, 3.5 mmol) and dry THF (20 mL) were added. The mixture was sonicated in an ultrasonic clean bath for 2 h. On completion of the reaction, the reaction mixture was allowed to stand overnight and filtered through a sintered funnel. The filtrate was concentrated under vacuum affording choline hydroxide as a viscous liquid. The residue was diluted with 10 mL of deionized water and treated by passing through a column charged with Amberlite® IRA910 anion exchange resin in order to remove residual halide. The solution of CBD (1 g, 3.2 mmol) in methanol (50 mL) was added to the obtained aqueous solution under vigorous stirring and heated at 60° C. for 4 h. The solvents were removed using a rotary evaporator. Viscous residue was dried under vacuum at 50° C. for 24 h to eliminate the residual water. The solid was washed with MTBE-heptane and dried in vacuum affording 1.15 g (86%) solid product. Mp 48-50° C. Structure of the resulting choline salt with CBD (1:1) was confirmed by proton NMR.

$^1$H NMR (400 MHz, DMSO-$d_6$): anion δ 6.0 (s, 2H), 5.0-4.95 (m, 1H), 4.4-4.3 (m, 2H), 3.6-3.3 (br. s., $H_2O$), 3.1-3.05 (m, 1H), 2.2-1.9 (m, 3H), 1.7-1.5 (m, 8H), 1.4-1.0 (m, 6H), 0.9-0.8 (m, 3H); cation δ 3.8-3.7 (m, 2H), 3.6-3.3 (br. s., $H_2O$), 3.1 (s, 9H).

Choline Salt with CBD (2:1)

To a 50-mL Erlenmeyer flask equipped with drying tube ($CaCl_2$) commercially available choline chloride (952 mg, 6.8 mmol), KOH (392 mg, 7 mmol) and dry THF (40 mL) were added. The mixture was sonicated in an ultrasonic clean bath for 2 h. On completion of the reaction, the reaction mixture was allowed to stand overnight and filtered through a sintered funnel. The filtrate was concentrated under vacuum affording choline hydroxide as a viscous liquid. The raw product was diluted with 10 mL of deionized water and treated by passing through a column charged with Amberlite® IRA910 anion exchange resin to remove residual halide. The solution of CBD (1 g, 3.2 mmol) in methanol (50 mL) was added to the obtained aqueous solution under vigorous stirring and heated at 60° C. for 4 h. The solvents were removed using a rotary evaporator. Viscous residue was dried under vacuum at 50° C. for 24 h to eliminate the residual water. The solid was washed with MTBE-heptane and dried in vacuum affording 1.25 g (75% yield) solid product. Mp. 58-60° C. Structure of the resulting choline salt with CBD (2:1) was confirmed by proton NMR.

$^1$H NMR (400 MHz, DMSO-$d_6$): anion δ 6.0 (s, 2H), 5.0-4.95 (m, 1H), 4.4-4.3 (m, 2H), 3.6-3.3 (br. s., $H_2O$), 3.1-3.05 (m, 1H), 2.2-1.9 (m, 3H), 1.7-1.5 (m, 8H), 1.4-1.0 (m, 6H), 0.9-0.8 (m, 3H); cation δ 3.8-3.7 (m, 4H), 3.6-3.3 (br. s., $H_2O$), 3.1 (s, 18H).

Choline Salt with THC (1:1)

Commercial aqueous 46% choline hydroxide solution (1.4 mL, 5 mmol) was added to a solution of Δ9-tetrahydrocannabinol (1 g, 3.2 mmol) in 20 mL of THF and stirred for 5 h. A mixture isopropanol/hexane (4:1, 20 mL) was added, and the mixture was stirred in dry ice/EtOH bath to induce the crystallization. Solidified product was filtered with suction, washed with 10 ml of chilled isopropanol and dried in vacuum to give the title compound, 1.1 g (82%). Mp. 35-44° C. Structure of the resulting choline salt with TCA (1:1) was confirmed by proton NMR.

$^1$H NMR (400 MHz, DMSO-d$_6$): anion δ: 6.3 (s, 1H), 6.1-6.0 (m, 2H), 3.6-3.3 (br. s, H$_2$O), 3.1-3.0 (m, 1H), 2.3-1.8 (m, 5H), 1.6 (s, 3H), 1.5-1.3 (m, 10H), 1.0 (s, 3H), 0.9-0.85 (m, 3H); cation δ 3.8-3.7 (m, 2H), 3.6-3.3 (br. s., H$_2$O), 3.1 (s, 9H).

Choline Salt with Tetrahydrocannabinolic Acid (2:1)

Commercial aqueous 46% choline hydroxide solution (1.7 mL, 6 mmol) was added to a solution of tetrahydrocannabinolic acid (1 g, 2.8 mmol) in 50 mL of THF, stirred for 5 h and evaporated in vacuum. Residual oil was triturated with MTBE and solidified product was washed with MTBE and dried in vacuum to give the title compound (1.31 g, 83%). Mp 65-69° C.

Choline Salt with Cannabidiolic Acid (3:1)

Commercial aqueous 46% choline hydroxide solution (2.6 mL, 9 mmol) was added to a solution of cannabidiolic acid (1 g, 2.8 mmol) in 50 mL of THF, stirred for 6 h and evaporated in vacuum. Residual oil was triturated with diethyl ether and solidified product was washed with diethyl ether and dried in vacuum to give the title compound (1.70 g, 91%). Mp 78-81° C.

L-Lysine Salt with CBD (1:1)

To a 50-mL Erlenmeyer flask equipped with drying tube (CaCl$_2$) L-lysine hydrochloride (620 mg, 3.4 mmol), KOH (196 mg, 3.5 mmol) and dry THF (20 mL) were added. The mixture was sonicated in an ultrasonic clean bath for 2 h. On completion of the reaction, the reaction mixture was allowed to stand overnight and filtered through a sintered funnel. The filtrate was concentrated under vacuum. The raw product was diluted with 10 mL deionized water and treated by passing through a column charged with Amberlite® IRA910 anion exchange resin to remove residual halide. The solution CBD (1 g, 3.2 mmol) in methanol (50 mL) was added to the obtained aqueous solution under vigorous stirring and heated at 60° C. for 4 h. The solvents were removed using a rotary evaporator. Viscous residue was dried under vacuum at 50° C. for 24 h to eliminate the residual water. The solid was washed with MTBE-heptane and dried in vacuum affording 1.25 g (85%) solid product. Mp. 56-60° C. Structure of the resulting lysine salt with CBD (1:1) was confirmed by proton NMR.

$^1$H NMR (400 MHz, DMSO-d$_6$): anion δ 6.0 (s, 2H), 5.0-4.95 (m, 1H), 4.4-4.3 (m, 2H), 3.6-3.3 (br. s., H$_2$O), 3.1-3.05 (m, 1H), 2.2-1.9 (m, 3H), 1.7-1.5 (m, 8H), 1.4-1.0 (m, 6H), 0.9-0.8 (m, 3H); cation δ 3.9-3.8 (m, 1H), 3.2-3.1 (m, 2H), 1.74-1.65 (m, 4H), 1.5-1.45 (m, 2H).

L-Lysine Salt with CBD (2:1)

To a 50-mL Erlenmeyer flask equipped with drying tube (CaCl$_2$) L-lysine hydrochloride (1.24 g, 6.8 mmol), KOH (302 mg, 7 mmol) and dry THF (40 mL) were added. The mixture was sonicated in an ultrasonic clean bath for 2 h. On completion of the reaction, the reaction mixture was allowed to stand overnight and filtered through a sintered funnel. The filtrate was concentrated under vacuum. The residue was diluted with 10 mL of deionized water and treated by passing through a column charged with Amberlite® IRA910 anion exchange resin to remove residual halide. The solution CBD (1 g, 3.2 mmol) in methanol (50 mL) was added to the obtained aqueous solution under vigorous stirring and heated at 60° C. for 4 h. The solvents were removed using a rotary evaporator. The viscous residue was dried under vacuum at 50° C. for 24 h to eliminate the residual water. The solid was washed with MTBE-heptane and dried in vacuum affording 1.45 g (75%) solid product. Mp. 200-210° C. Structure of the lysine salt with CBD (2:1) was confirmed by proton NMR.

$^1$H NMR (400 MHz, DMSO-d$_6$): anion δ 6.0 (s, 2H), 5.05-5.0 (m, 1H), 4.4-4.3 (m, 2H), 4.2-3.0 (br. s., H$_2$O), 2.2-1.9 (m, 3H), 1.7-1.5 (m, 8H), 1.4-1.0 (m, 6H), 0.9-0.8 (m, 3H); cation δ 3.2-3.1 (m, 4H), 1.74-1.65 (m, 8H), 1.5-1.45 (m, 4H).

L-Lysine Salt with THC (1:1)

To a 50-mL Erlenmeyer flask equipped with drying tube (CaCl$_2$) L-lysine hydrochloride (620 mg, 3.4 mmol), KOH (196 mg, 3.5 mmol) and dry THF (20 mL) were added. The mixture was sonicated in an ultrasonic clean bath for 2 h. On completion of the reaction, the reaction mixture was allowed to stand overnight and filtered through a sintered funnel. The filtrate was concentrated under vacuum. The residue was diluted with 10 mL of deionized water and then treated by passing through a column charged with Amberlite® IRA910 anion exchange resin to remove residual halide. The solution Δ$^9$-tetrahydrocannabinol (1 g, 3.2 mmol) in methanol (50 mL) was added to the obtained aqueous solution under vigorous stirring and heated at 60° C. for 4 h. The solvents were removed using a rotary evaporator. The viscous residue was dried under vacuum at 50° C. for 24 h to eliminate the residual water. The solid was washed with MTBE-heptane and dried in vacuum affording 0.79 g (54%) solid material. Mp. 65-69° C. Structure of the lysine salt with THC (1:1) was confirmed by proton NMR.

$^1$H NMR (400 MHz, DMSO-d$_6$): anion δ: 6.3 (s, 1H), 6.1-6.0 (m, 2H), 4.0-3.3 (br. s, H$_2$O), 3.1-3.0 (m, 1H), 2.3-1.8 (m, 5H), 1.6 (s, 3H), 1.5-1.3 (m, 10H), 1.0 (s, 3H), 0.9-0.85 (m, 3H); cation δ 3.2-3.1 (m, 2H), 1.74-1.65 (m, 4H), 1.5-1.4 (m, 2H).

Trometamine Salt with CBD (1:1)

To a 50-mL Erlenmeyer flask equipped with drying tube (CaCl$_2$) tris(hydroxymethyl)aminomethane hydrochloride (540 mg, 3.4 mmol), KOH (196 mg, 3.5 mmol) and dry THF (20 mL) were added. The mixture was sonicated in an ultrasonic clean bath for 2 h. On completion of the reaction, the reaction mixture was allowed to stand overnight and filtered through a sintered funnel. The filtrate was concentrated under vacuum. The residue was diluted with 10 mL of deionized water and treated by passing through a column charged with Amberlite® IRA910 anion exchange resin to remove residual halide. The solution CBD (1 g, 3.2 mmol) in methanol (50 mL) was added to the obtained aqueous solution under vigorous stirring and heated at 60° C. for 4 h. The solvents were removed using a rotary evaporator. Viscous residue was dried under vacuum at 50° C. for 24 h to eliminate the residual water. The solids were washed with MTBE-heptane and dried in vacuum affording 1.15 g (86%)

solid product. Mp. 125-131° C. Structure of the trometamine salt with CBD (1:1) was confirmed by proton NMR.

$^1$H NMR (400 MHz, DMSO-d$_6$): anion δ 6.1 (s, 2H), 5.2-5.15 (m, 1H), 4.5-4.3 (m, 2H), 3.7-3.0 (br. s., H$_2$O), 2.2-1.9 (m, 3H), 1.7-1.5 (m, 8H), 1.4-1.1 (m, 6H), 1.0-0.9 (m, 3H); cation δ 3.35 (s, 6H).

Trometamine Salt with CBD (2:1)

To a 50-mL Erlenmeyer flask equipped with drying tube (CaCl$_2$) tris(hydroxymethyl)aminomethane hydrochloride (1.08 g, 6.8 mmol), KOH (392 mg, 7 mmol) and dry THF (40 mL) were added. The mixture was sonicated in an ultrasonic clean bath for 2 h. On completion of the reaction, the reaction mixture was allowed to stand overnight and filtered through a sintered funnel. The filtrate was concentrated under vacuum. The raw product was diluted with 10 mL of deionized water and treated by passing through a column charged with Amberlite® IRA910 anion exchange resin to remove residual halide. The solution CBD (1 g, 3.2 mmol) in methanol (50 mL) was added to the obtained aqueous solution under vigorous stirring and heated at 60° C. for 4 h. The solvents were removed using a rotary evaporator. The viscous residue was dried under vacuum at 50° C. for 24 h to eliminate the residual water. The solid was washed with MTBE-heptane and dried in vacuum affording 1.46 g (82%) solid product. Mp 148-150° C. Structure of the trometamine salt with CBD (2:1) was confirmed by proton NMR.

$^1$H NMR (400 MHz, DMSO-d$_6$): anion δ 6.0 (s, 2H), 5.0-4.95 (m, 1H), 4.5-4.4 (m, 2H), 3.7-3.0 (br. s., H$_2$O), 2.2-1.9 (m, 3H), 1.7-1.5 (m, 8H), 1.4-1.1 (m, 6H), 1.0-0.9 (m, 3H); cation δ 3.3 (s, 12H).

Meglumine Salt with CBD (1:1)

To a 50-mL Erlenmeyer flask equipped with drying tube (CaCl$_2$)N-methyl-D-glucamine hydrochloride (780 mg, 3.4 mmol), KOH (196 mg, 3.5 mmol), and dry THF (20 mL) were added. The mixture was sonicated in an ultrasonic clean bath for 2 h. On completion of the reaction, the reaction mixture was allowed to stand overnight and filtered through a sintered funnel. The filtrate was concentrated under vacuum. The raw product was diluted with 10 mL of deionized water and treated by passing through a column charged with Amberlite® IRA910 anion exchange resin to remove residual halide. The solution CBD (1 g, 3.2 mmol) in methanol (50 mL) was added to the obtained aqueous solution under vigorous stirring and heated at 60° C. for 4 h. The solvents were removed using a rotary evaporator. The viscous residue was dried under vacuum at 50° C. for 24 h to eliminate the residual water. The solid was washed with MTBE-heptane and dried in vacuum affording 1.25 g (77%) solid product. Mp. 50-52° C. Structure of the meglumine salt with CBD (1:1) was confirmed by proton NMR.

$^1$H NMR (400 MHz, DMSO-d$_6$): anion δ 6.2 (s, 2H), 5.2-5.1 (m, 1H), 4.6-4.5 (m, 2H), 3.8-3.4 br. s., H$_2$O), 2.4-2.0 (m, 3H), 1.9-1.7 (m, 8H), 1.6-1.2 (m, 6H), 1.1-0.95 (m, 3H); cation δ 3.8-3.7 (m, 4H), 2.7-2.6 (m, 5H).

Meglumine Salt with CBD (2:1)

To a 50-mL Erlenmeyer flask equipped with drying tube (CaCl$_2$)N-methyl-D-glucamine hydrochloride (1.56 g, 6.8 mmol), KOH (392 mg, 7 mmol) and dry THF (40 mL) were added. The mixture was sonicated in an ultrasonic clean bath for 2 h. On completion of the reaction, the reaction mixture was allowed to stand overnight and filtered through a sintered funnel. The filtrate was concentrated under vacuum. The raw product was diluted with 10 mL of deionized water and treated by passing through a column charged with Amberlite® IRA910 anion exchange resin to remove residual halide. The solution CBD (1 g, 3.2 mmol) in methanol (50 mL) was added to the obtained aqueous solution under vigorous stirring and heated at 60° C. for 4 h. The solvents were removed using a rotary evaporator. The viscous residue was dried under vacuum at 50° C. for 24 h to eliminate the residual water. The solid was washed with MTBE-heptane and dried in vacuum affording 1.85 g (82%) solid product. Mp 115-117° C. Structure of the resulting meglumine salt with CBD (2:1) was confirmed by proton NMR.

$^1$H NMR (400 MHz, DMSO-d$_6$): anion δ 6.4 (s, 2H), 5.3-5.2 (m, 1H), 4.7-4.6 (m, 2H), 3.7-3.3 br. s., H$_2$O), 2.4-2.0 (m, 3H), 1.9-1.7 (m, 8H), 1.6-1.2 (m, 6H), 1.1-0.95 (m, 3H); cation δ 3.8-3.7 (m, 8H), 2.8-2.7 (m, 10H).

Meglumine Salt with THC (1:1)

To a 50-mL Erlenmeyer flask equipped with drying tube (CaCl$_2$)N-methyl-D-glucamine hydrochloride (780 mg, 3.4 mmol), KOH (196 mg, 3.5 mmol), and dry THF (20 mL) were added. The mixture was sonicated in an ultrasonic clean bath for 2 h. On completion of the reaction, the reaction mixture was allowed to stand overnight and filtered through a sintered funnel. The filtrate was concentrated under vacuum. The raw product was diluted with 10 mL of deionized water and treated by passing through a column charged with Amberlite® IRA910 anion exchange resin to remove residual halide. The solution Δ$^9$-tetrahydrocannabinol (1 g, 3.2 mmol) in methanol (50 mL) was added to the obtained aqueous solution under vigorous stirring and heated at 60° C. for 4 h. The solvents were removed using a rotary evaporator. The viscous residue was dried under vacuum at 50° C. for 24 h to eliminate the residual water. The solid was washed with MTBE-heptane and dried in vacuum affording 1.1 g (68%) solid product. Mp. 60-62° C. Structure of the resulting meglumine salt with THC (1:1) was confirmed by proton NMR.

$^1$H NMR (400 MHz, DMSO-d$_6$): anion δ: 6.3 (s, 1H), 6.1-6.0 (m, 2H), 3.8-3.1 (br. s, H$_2$O), 3.1-3.0 (m, 1H), 2.3-1.8 (m, 5H), 1.6 (s, 3H), 1.5-1.3 (m, 10H), 1.0 (s, 3H), 0.9-0.85 (m, 3H); cation δ 3.8-3.7 (m, 4H), 2.7-2.6 (m, 5H).

Meglumine Salt with Tetrahydrocannabinolic Acid (2:1)

To a 50-mL Erlenmeyer flask equipped with drying tube (CaCl$_2$)N-methyl-D-glucamine hydrochloride (1.38 g, 6 mmol), KOH (337 mg, 6 mmol), and dry THF (50 mL) were added. The mixture was sonicated in an ultrasonic clean bath for 2 h. On completion of the reaction, the reaction mixture was allowed to stand overnight and filtered through a sintered funnel. The filtrate was concentrated under vacuum. The crude residue was diluted with 10 mL of deionized water and treated by passing through a column charged with Amberlite® IRA910 anion exchange resin in order to remove residual halide. The solution tetrahydrocannabinolic acid (1 g, 2.8 mmol) in methanol (50 mL) was added to the obtained aqueous solution under vigorous stirring and heated at 60° C. for 4 h. The solvents were removed in vacuum using a rotary evaporator. The viscous residue was dried in vacuum at 50° C. for 24 h to eliminate the residual water. The residual viscous oil was triturated with MTBE.

The solidified product was washed with MTBE and dried in vacuum affording 1.9 g (91%) desired product. Mp 96-101° C.

Procaine Salt with CBD (1:1)

To a 50-mL Erlenmeyer flask equipped with drying tube (CaCl$_2$) procaine hydrochloride (920 mg, 3.4 mmol), KOH (196 mg, 3.5 mmol), and dry THF (20 mL) were added. The mixture was sonicated in an ultrasonic clean bath for 2 h. On completion of the reaction, the reaction mixture was allowed to stand overnight and filtered through a sintered funnel. The filtrate was concentrated under vacuum. The residue was diluted with 10 mL of deionized water and treated by passing through a column charged with Amberlite® IRA910 anion exchange resin in order to remove residual halide. The solution CBD (1 g, 3.2 mmol) in methanol (50 mL) was added to the obtained aqueous solution under vigorous stirring and heated at 60° C. for 4 h. The solvents were removed using a rotary evaporator. A viscous residue was dried in vacuum at 50° C. for 24 h to eliminate the water. The solid was washed with MTBE-heptane and dried in vacuum affording 1.46 g (83%) solid product. Mp. 44-43° C.

Procaine Salt with CBD (2:1)

To a 50-mL Erlenmeyer flask equipped with drying tube (CaCl$_2$) procaine hydrochloride (1.84 mg, 6.8 mmol), KOH (392 mg, 7 mmol) and dry THF (40 mL) were added. The mixture was sonicated in an ultrasonic clean bath for 2 h. On completion of the reaction, the reaction mixture was allowed to stand overnight and filtered through a sintered funnel. The filtrate was concentrated under vacuum. The residue was diluted with 10 mL of deionized water and treated by passing through a column charged with Amberlite® IRA910 anion exchange resin in order to remove residual halide. The solution CBD (1 g, 3.2 mmol) in methanol (50 mL) was added to the obtained aqueous solution under vigorous stirring and heated at 60° C. for 4 h. The solvents were removed using a rotary evaporator. A viscous residue was dried in vacuum at 50° C. for 24 h to eliminate the water. The solid was washed with MTBE-heptane and dried in vacuum affording 1.85 g (74%) solid product. Mp. 48-50° C.

Arginine Salt with CBD (1:1)

Arginine (0.56 g, 3.2 mmol) was added to a solution of CBD (1 g, 3.2 mmol) in 50 mL of ethanol and stirred for 2 h. Ethanol was removed in vacuum. The residue was washed with 3×25 ml of hexane/MTBE and dried in vacuum. Yield: 1.25 g (80%). Mp. 148-150° C.

Arginine Salt with CBD (2:1)

Arginine (1.12 g, 6.4 mmol) was added to a solution of CBD (1 g, 3.2 mmol) in 100 ml of ethanol and stirred for 3 h. Ethanol was removed in vacuum. The residue was washed with 3×25 ml of hexane/MTBE and dried in vacuum. Yield: 1.8 g (85%). Mp. 156-158° C.

1-Benzylpyridinium Salt with Cannabigerol (1:1)

A: 1-Benzylpyridin-1-ium Chloride

Benzyl chloride (35.7 mL, 0.31 mol) was added drop wise to a solution of pyridine (25.0 mL, 0.31 mol) in toluene (100 mL) in an ice bath and stirred for one hour. Precipitate was filtered with suction and dried in vacuum.

B: 1-Benzylpyridinium cannabigerol salt (1:1)

Sodium methoxide 25% solution in methanol (37 μL, 0.15 mmol) was added to the solution of 1-benzylpyridin-1-ium chloride (6 mg, 0.3 mmol) and cannabigerol (50 mg, 0.15 mmol) in methanol (10 mL). The reaction mixture stirred for 1 h and evaporated in vacuum. Residue was dispersed in water (2 mL) and extracted with dichloromethane. Organic layer evaporated in vacuum giving a desired product as sticky oil in quantitative yield.

Tetraethylammonium Salt with CBD (2:1)

An aqueous solution 25% of Et$_4$NOH (2.4 mL, 6.5 mmol) was added to a solution of cannabidiol (1 g, 3.2 mmol) in 20 mL of MeOH and heated at 50° C. for 2 h. The solvents were evaporated in vacuum. The residue, white solid was dried in vacuum giving the desired salt in quantitative yield.

Benzyltrimethylammonium Salt with CBD (1:1)

Benzyltrimethylammonium methoxide 40 wt. % solution in methanol (1.5 mL, 3.2 mmol) was added to a solution of cannabidiol (1 g, 3.2 mmol) in 20 mL of MeOH. The mixture stirred for 1 h and evaporated in vacuum obtaining desired product as sticky oil in a quantitative yield.

Agmatine Salt with THC (1:1)

Agmatine (417 mg, 3.2 mmol) was added to a solution of $\Delta^9$-tetrahydrocannabinol (1 g, 3.2 mmol) in 20 mL of THF and stirred for 30 min. THF was removed in vacuum affording desired salt in a quantitative yield.

Tetrakis(2-Hydroxyethyl)Ammonium Salt with $\Delta^9$-Tetrahydrocannabivarin (1:1)

A. Tetrakis(2-Hydroxyethyl) Ammonium Bromide

Triethanolamine (1 g, 6.77 mmol) was mixed with 2-bromoethanol (0.84 g, 6.77 mmol) and stirred for 5 days at 70° C. by using a hot plate with a silicon bath. After that the magnetic stirrer was removed from the reaction vial and the vial was placed in an oven at 70° C. for 5 more days. After cooling in a fridge to 5° C. the salt solidified into a waxy-like white solid.

B. Tetrakis (2-Hydroxyethyl) Ammonium Hydroxide

Chemical exchange of bromine by hydroxide anions was performed by using a column exchange containing a strongly basic resin (AmberChrom® 1×8, Sigma-Aldrich). The basic resin was first activated with 250 ml of an aqueous solution of 1M KOH followed by 250 ml of deionized water. The aqueous solution containing 1.8 g of tetrakis(2-hydroxyethyl) ammonium bromide from previous step was flushed three times through the column being activated every time before flushing. The solvent was removed in vacuum. The residue, the hydroxide salt dried at 70° C. in vacuum for 48 hours and stored in a refrigerator at 4° C. until solidified.

C. Tetrakis(2-hydroxyethyl)ammonium Salt with
Δ⁹-Tetrahydrocannabivarin (1:1)

Tetrakis (2-hydroxyethyl) ammonium hydroxide (417 mg, 3.2 mmol) obtained from previous step was added to a solution of Δ⁹-tetrahydrocannabivarin (100 mg, 0.35 mmol) in 20 mL of dry EtOH and stirred for 30 min. The solvent was removed under reduced pressure. The residue was dried in vacuum at 70° C. for 48 hours affording desired salt in a quantitative yield.

Tetrabutylammonium Salt with
Δ⁹-Tetrahydrocannabivarin (1:1)

Δ⁹-Tetrahydrocannabivarin (100 mg, 0.35 mmol) was dissolved in 20 mL of acetonitrile at room temperature. The tetrabutylammonium hydroxide 30-hydrate (400 mg, 0.5 mmol) was added and the mixture was stirred vigorously for 3 h. The resulting reaction mixture was concentrated in vacuum. The residue was extracted twice with dichloromethane. Combined organic layers were washed with deionized water to remove excess of tetrabutylammonium hydroxide, dried over $Na_2SO_4$, evaporated in vacuum to afford desired salt as sticky brown oil quantitatively.

Tetraethylammonium Salt with Cannabinol (1:1)

A mixture of cannabinol (1 g, 3.2 mmol), anhydrous K2CO3 (5.0 g) and tetraethylammonium bromide (2 g) in benzene (50 mL) was heated under reflux for 5 h. The mixture was filtered off to remove any impurities and non-reacted material. The filtrate was evaporated to almost dryness. The viscous residue was treated with 20 ml methanol and left overnight in a fridge at −20° C. The colorless crystals that formed were filtered off and dried in vacuum. Yield: 90%.

Quinine Salt with Cannabinol (1:1)

A mixture of quinine hydrochloride dihydrate (1.35 g) and Ambertlist® A26 (hydroxide form) (10 g) in methanol (50 mL) was stirred at room temperature overnight. The insoluble material was filtered off through celite and washed with methanol (20 ml). To the filtrate, cannabinol (1 g, 3.2 mmol) was added and stirred for 5 h. The solvent was evaporated in vacuum. The oily residue was triturated with diethyl ether. The precipitated solid was collected by filtration, washed with diethyl ether and dried in vacuum to give the title compound. Yield: 1.9 g.

Acetylcholine Salt with Cannabinol (1:1)

A mixture of acetylcholine chloride (636 mg) and Ambertlist® A26 (hydroxide form) (10 g) in methanol (50 mL) was stirred at room temperature overnight. The insoluble material was filtered off through celite and washed with methanol (20 ml). To the filtrate, cannabinol (1 g, 3.2 mmol) was added and stirred for 5 h. The solvent was evaporated in vacuum. The oily residue was triturated with diethyl ether. The precipitated solid was collected by filtration, washed with diethyl ether and dried in vacuum to give the title compound. Yield: 1.3 g.

The results of the solubility of the synthesized salts in water are given in Table 1. From the data comparison, a thousandfold increase in solubility is observed, as for example in the case of CBD and THC.

TABLE 1

Water Solubility of Cannabinoid Salts.

| Cannabinoid | Base | Ratio Cannabinoid/Base | Solubility, mg/mL |
|---|---|---|---|
| [CBD structure] | — | — | 0.0007[a] |
| | HO-CH₂CH₂-NMe₃⁺ | 1:1<br>1:2 | 6<br>10 |
| | H₂N-(CH₂)₄-CH(NH₃⁺)-COO⁻ (lysine) | 1:1<br>1:2 | 2<br>4 |
| | (HOCH₂)₃C-NH₂ (tris) | 1:1<br>1:2 | 5<br>6 |

TABLE 1-continued
Water Solubility of Cannabinoid Salts.
| Cannabinoid | Base | Ratio Cannabinoid/Base | Solubility, mg/mL |
|---|---|---|---|
| |  (N-methylglucamine) | 1:1<br>1:2 | 15<br>8 |
| |  (procaine) | 1:1<br>1:2 | 5<br>6 |
| |  (arginine) | 1:1<br>1:2 | 3<br>2 |
| | Et$_4$N$^+$ | 1:2 | 0.1 |
| |  (benzyltrimethylammonium) | 1:1 | 0.4 |
| 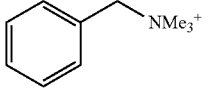 | — | — | 0.0028[b] |
| | HO\~\~NMe$_3^+$ (choline) | 1:1 | 3 |
| |  (lysine) | 1:1 | 2 |
| |  (N-methylglucamine) | 1:1 | 9 |
| |  (agmatine) | 1:1 | 0.2 |
| 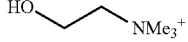 | — | — | 2.2[c] |

TABLE 1-continued

Water Solubility of Cannabinoid Salts.

| Cannabinoid | Base | Ratio Cannabinoid/Base | Solubility, mg/mL |
|---|---|---|---|
| [THCA structure] | HO~NMe₃⁺ | 1:3 | 24 |
| | — | — | 0.048[d] |
| | HO~NMe₃⁺ | 1:2 | 20 |
| | meglumine (MeNH-CH₂(CHOH)₄-CH₂OH) | 1:2 | 20 |
| [CBD structure] | — | — | 0.005[e] |
| | N-benzylpyridinium | 1:1 | 1 |
| | — | — | 0.009[f] |
| [THC-propyl structure] | N(CH₂CH₂OH)₄⁺ | 1:1 | 7 |
| | n-Bu₄N⁺ | 1:1 | 0.2 |
| [CBN-like structure] | — | — | insoluble |
| | Et₄N⁺ | 1:1 | 0.2 |

TABLE 1-continued

Water Solubility of Cannabinoid Salts.

| Cannabinoid | Base | Ratio Cannabinoid/Base | Solubility, mg/mL |
|---|---|---|---|
| | 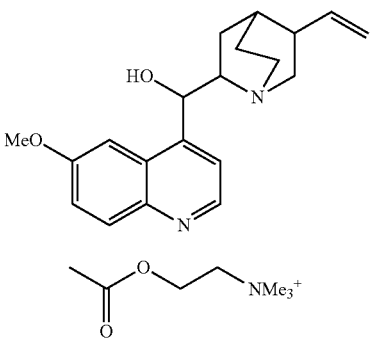 | 1:1 | 0.1 |
| | 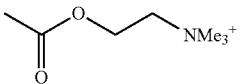 | 1:1 | 1 |

[a] E. Samara, M. Bialer *Drug Metab. Dispos.* 16, 875-879 (1988);
[b] E. R. Garrett, C. A. Hunt *J. Pharm. Sci.* 63, 1056-1064 (1974);
[c] https://www.linkedin.com/pulse/bioavailability-cbd-vs-cbda-rob-wohleb-phd?trk=public_profile_article_view;
[d] Hazekamp A., Bastola K., Rashidi H., et al. J Ethnopharmacol. 113, 85-90 (2007);
[e] https://go.drugbank.com/drugs/DB14734;
[f] https://go.drugbank.com/drugs/DB11755.

The invention claimed is:

1. A water-soluble salt of cannabinoid compound of Formula (I)

Formula (I)

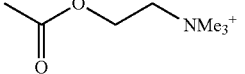

wherein B is selected from the group selected from the group consisting of $C_3H_7$ (n-propyl) or $C_5H_{11}$ (n-pentyl) and the combination of A, B, D and R of moiety C form a cannabinoid, wherein the cannabinoid is selected from the group consisting of Formula (Ia)

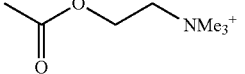

cannabidiol (CBD)

Formula (Ib)

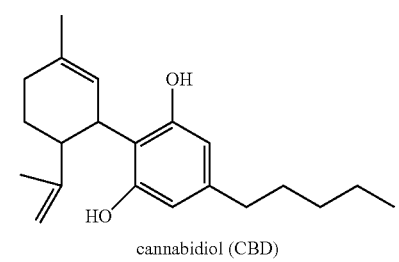

cannabigerol (CBG)

Formula (Ic)

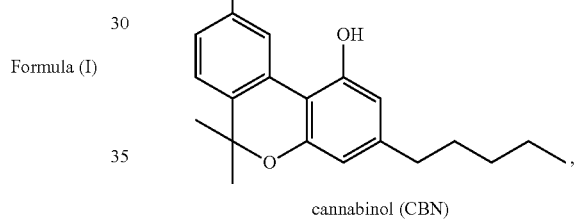

cannabinol (CBN)

Formula (Id)

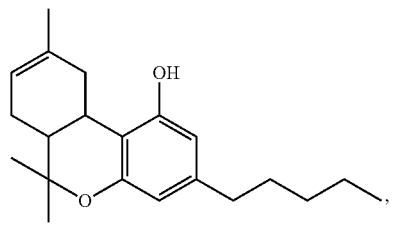

Δ⁸-tetrahyrdocannabinol (Δ⁸-THC)

Formula (Ie)

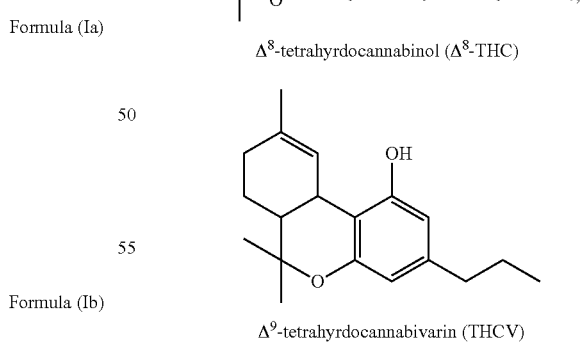

Δ⁹-tetrahyrdocannabivarin (THCV)

including stereoisomers thereof and a mixture thereof, and $X^+$ is selected from the group consisting of tetraethylammonium, tetrabutylammonium, benzyltrimethylammonium, 1-benzylpyridinium, tetrakis(2-hydroxyethyl)ammonium, tris(hydroxymethyl) methylammonium, N-methyl-D-glucammonium, procainium, quininium, agmatinium, metforminium, cholinium, acetylcholinium, meldonium and quaternary ion of arginine and lysine.

2. Process for the preparation of compounds of claim 1 comprising deprotonation of the phenolic hydroxyl group of cannabinoid formula (Ia-e) by addition of base.

\* \* \* \* \*